United States Patent

Sotani et al.

[11] Patent Number: 5,858,408
[45] Date of Patent: Jan. 12, 1999

[54] SUSTAINED-RELEASE ORAL OINTMENT

[75] Inventors: Sadao Sotani, Toyama; Shosaku Kato, Himi; Yasuo Watanabe; Isamu Takakura, both of Toyama, all of Japan

[73] Assignee: Toyama Chemical Co., Ltd., Tokyo, Japan

[21] Appl. No.: 765,446
[22] PCT Filed: Jul. 20, 1994
[86] PCT No.: PCT/JP94/01191
  § 371 Date: Jan. 17, 1997
  § 102(e) Date: Jan. 17, 1997
[87] PCT Pub. No.: WO96/02275
  PCT Pub. Date: Feb. 1, 1996
[51] Int. Cl.⁶ ...................................................... A61K 9/14
[52] U.S. Cl. ............................................ 424/489; 424/682
[58] Field of Search ...................................... 424/489, 682

[56] References Cited

U.S. PATENT DOCUMENTS

| | | |
|---|---|---|
| 4,704,459 | 11/1987 | Todo et al. . |
| 4,996,197 | 2/1991 | Mazuel . |
| 5,248,504 | 9/1993 | Friedman ................................ 424/489 |
| 5,260,073 | 11/1993 | Phipps . |
| 5,366,733 | 11/1994 | Brizzolara et al. . |
| 5,478,578 | 12/1995 | Arnold et al. ........................... 424/489 |
| 5,603,943 | 2/1997 | Yanagawa ............................... 424/489 |
| 5,629,011 | 5/1997 | Illum ....................................... 424/489 |

FOREIGN PATENT DOCUMENTS

| | | |
|---|---|---|
| 0 256 611 | 2/1988 | European Pat. Off. . |
| 0 291 838 | 11/1988 | European Pat. Off. . |
| 2 239 355 | 2/1974 | Germany . |

OTHER PUBLICATIONS

Patent Abstracts of Japan, vol. 015, No. 221 (C–838), Jun. 6, 1991 & JP 03 066612 A (Sato Seiyaku KK), Mar. 22, 1991, Abstract.

Patent Abstracts of Japan, vol. 17, No. 367 (C–1082), Jul. 12, 1993 & JP 05 058895 A (Toyama Chem Co Ltd), Mar. 9, 1993, Abstract.

Patent Abstracts of Japan, vol. 12, No. 467 (C–550), Dec. 7, 1988 & JP 63 188626 A (Dainippon Pharmaceut Co Ltd), Aug. 4, 1988, Abstract.

The Merck Index 1989 p. 1504.

*Primary Examiner*—Joseph L. Schofer
*Assistant Examiner*—N. Sarofin
*Attorney, Agent, or Firm*—Oblon, Spivak, McClelland, Maier & Neustadt, P.C.

[57] ABSTRACT

The preent invention relates to a sustained-release oral ointment which comprises a hydrophobic ointment base, an adhesive substance, an aluminum compound and a drug. The ointment is useful as a sustained-release oral ointment which has applicability to an oral mucosa, particularly to a peridontal pocket, sustained-release properties to supply a drug to affected part over a long period of time while maintaining the concentration thereof at a sufficiently high level, and enhanced ratio of utilization of drug (the ratio of the total amount of drug released to affected part to the total amount of drug in the ointment applied).

2 Claims, 3 Drawing Sheets

FIG. 1
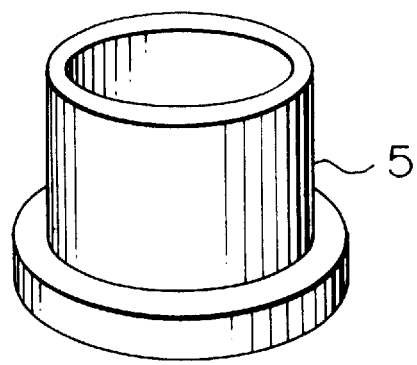
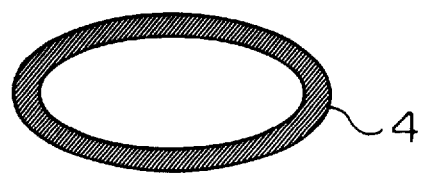
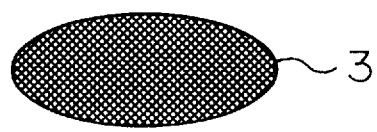
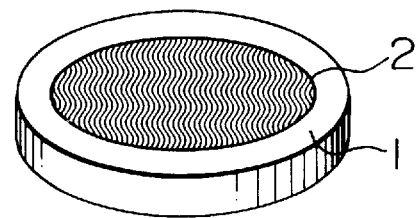

SUSTAINED-RELEASE ORAL OINTMENT

TECHNICAL FIELD

The present invention relates to a sustained-release oral ointment which is intended for use in the remedy of oral diseases, such as periodontal disease and the like. More particularly, the present invention relates to a sustained-release oral ointment which comprises a hydrophobic ointment base, an adhesive substance, an aluminum compound and a drug.

BACKGROUND ART

As ointment bases applied on oral mucosa, there are generally and widely used those ointments comprising a hydrophobic ointment base (e.g. petrolatum or plastibase) and an adhesive substance (e.g. sodium carboxymethyl cellulose or sodium polyacrylate) in consideration of the action of saliva [Kenalog for Use in Oral Cavity (trade name), a product of SQUIBB JAPAN INC.; Aphtasolon for Dental Use (or for Use in Oral Cavity, trade name), a product of Showa Yakuhin Kako Co., Ltd.; and Dexarutin Ointment (trade name), a product of Nippon Kayaku Co., Ltd.]. These ointments, however, have been insufficient as sustained-release ointments. The inventors of the present application have previously filed JP-A-4-13616 in which they have disclosed a sustained-release oral ointment which comprises a hydrophobic ointment base, an adhesive substance, a polyhydric alcohol and a drug. However, there has not yet been known an ointment base which comprises a hydrophobic ointment base, an adhesive substance and an aluminum compound.

Therefore, it has been desired to develop a sustained-release oral ointment which has applicability to an oral mucosa, particularly to a periodontal pocket, sustained-release properties to supply a drug to affected part over a long period of time while maintaining the concentration thereof at a sufficiently high level, and enhanced ratio of utilization of drug (the ratio of the total amount of drug released to affected part to the total amount of drug in the composition applied).

Hence, in order to solve the above problems, the present invention has an object of providing a novel sustained-release oral ointment.

DISCLOSURE OF THE INVENTION

Under the above-mentioned situation, the inventors of the present application made an intensive study. As a result, the present inventors found that a sustained-release oral ointment which comprises a hydrophobic ointment base, an adhesive substance, an aluminum compound and a drug can achieve the above object, and completed the present invention.

The present invention is hereinafter described in detail.

The drug used in the present invention is not particularly restricted. Specific examples thereof includes antibacterial agents such as compounds represented by the following general formula [I]:

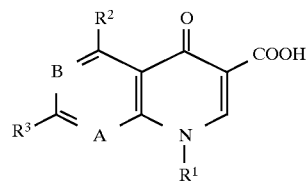

wherein $R^1$ represents a substituted or unsubstituted alkyl, alkenyl, cycloalkyl, aryl or heterocyclic group; $R^2$ represents a hydrogen atom, a halogen atom, an alkyl group, an alkoxy group, a protected or unprotected hydroxyl, amino or alkylamino group, or a dialkylamino group; $R^3$ represents a substituted or unsubstituted cycloalkyl, vinyl or cyclic amino group;

represents a group

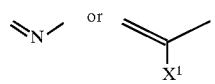

wherein $X^1$ represents a hydrogen atom or a halogen atom, or alternatively, forms, together with $R^1$, a group represented by the formula:

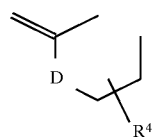

wherein $R^4$ represents a hydrogen atom or an alkyl group, and D represents an oxygen atom or a sulfur atom; and

represents a group represented by

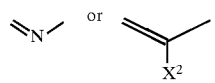

wherein $X^2$ represents a hydrogen atom or a halogen atom, salts thereof, tetracycline, oxytetracycline, fradiomycin sulfate, chloramphenicol and the like; bactericidal disinfectants such as chlorhexidine hydrochloride, cetylpyridinium chloride, benzethonium chloride, decalinium chloride, benzalkonium chloride and the like; antiphlogistics such as dexamethasone, triamcinolone acetonide, sodium azulenesulfonate and the like; antiphlogistic enzyme preparation such as α-amylase and the like; local anesthetics such as lidocaine, ethyl aminobenzoate and the like; and so forth.

In the specification of the present application, unless otherwise specified, "halogen atom" refers to a fluorine atom, a chlorine atom, a bromine atom or an iodine atom; "alkyl group" refers to $C_{1-10}$ alkyl groups such as methyl, ethyl, n-propyl, isopropyl, n-butyl, isobutyl, sec-butyl, tert-butyl, pentyl, hexyl, octyl and the like; "alkoxy group" refers to, for example, —O-alkyl groups (the alkyl group thereof refers to the above-mentioned $C_{1-10}$ alkyl group); "alkylamino group" refers to $C_{1-10}$ alkylamino groups such as methylamino, ethylamino, propylamino and the like; "dialkylamino group" refers to di-$C_{1-10}$alkylamino groups such as dimethylamino and the like; "alkenyl group" refers to $C_{2-10}$ alkenyl groups such as vinyl, allyl, 1-propenyl, 1-butenyl and the like; "cycloalkyl group" refers to $C_{3-10}$ cycloalkyl groups such as cyclopropyl, cyclobutyl, cyclopentyl, cyclohexyl and the like; "aryl group" refers to groups having aromaticity such as phenyl, naphthyl and the like; "alkoxycarbonyl group" refers to, for example, —COO-alkyl groups (the alkyl group thereof refers to the above-mentioned $C_{1-10}$ alkyl group); "hydroxyalkyl group" refers to hydroxy-$C_{1-10}$ alkyl groups such as hydroxymethyl, hydroxyethyl, hydroxypropyl and the like; "aminoalkyl group" refers to amino-$C_{1-10}$ alkyl groups such as aminomethyl, aminoethyl, aminopropyl and the like; "alkylaminoalkyl group" refers to $C_{1-10}$-alkylamino-$C_{1-10}$ alkyl groups such as methylaminomethyl, ethylaminomethyl, ethylaminoethyl and the like; "dialkylaminoalkyl group" refers to di-$C_{1-10}$-alkylamino-$C_{1-10}$ alkyl groups such as dimethylaminomethyl, diethylaminomethyl and the like; "cyclic amino group" refers to four- to ten-membered cyclic amino groups such as piperazinyl, pyrrolidinyl, morpholinyl, 1,4-diazabicyclo[3.2.1]octyl and the like; "cyclic aminoalkyl group" refers to four- to six-membered cyclic amino-$C_{1-10}$ alkyl groups such as 1-piperazinylmethyl, 1-pyrrolidinylmethyl, 1-azetidinylmethyl, 1-morpholinylmethyl and the like; "acylamino group" refers to $C_{1-10}$ acylamino groups such as formylamino, acetylamino, propionylamino, butyrylamino and the like; "acyloxy group" refers to $C_{1-10}$ acyloxy groups such as formyloxy, acetyloxy, propionyloxy, butyryloxy and the like; "trihalogeno-lower alkyl group" refers to trihalogeno-$C_{1-10}$ alkyl groups such as trichloromethyl, trifluoromethyl and the like; and "heterocyclic group" refers to five- or six-membered rings containing at least one heteroatom selected from oxygen atom, nitrogen atom and sulfur atom, or fused rings thereof, for example, groups such as furyl, pyrrolyl, thienyl, oxazolyl, imidazolyl, thiazolyl, 1-pyrrolidinyl, benzofuryl, benzothiazolyl, pyridyl, quinolyl, pyrimidinyl, morpholinyl and the like.

In the compounds of general formula [I] or salts thereof, each of the groups represented by $R^1$ may be substituted with at least one substituent selected from a halogen atom, a cyano group, a protected or unprotected carboxy group, a protected or unprotected hydroxyl group, a protected or unprotected amino group, an alkyl group, an alkoxy group, an alkoxycarbonyl group, an aryl group, a cycloalkyl group, an acylamino group, an acyloxy group, an alkenyl group, a trihalogenoalkyl group, an alkylamino group, a dialkylamino group, and so forth; and each of the groups represented by $R^3$ may be substituted with at least one substituent selected from a halogen atom, an alkyl group, a protected or unprotected carboxy group, a protected or unprotected hydroxyl group, a protected or unprotected amino group, a protected or unprotected alkylamino group, a protected or unprotected aminoalkyl group, a protected or unprotected alkylaminoalkyl group, a protected or unprotected hydroxyalkyl group, a dialkylamino group, a dialkylaminoalkyl group, a cyclic aminoalkyl group, and so forth.

The carboxy-protecting group includes, for example, pharmaceutically acceptable carboxy-protecting groups such as ester-forming group easily eliminated in living body. Specific examples thereof are lower alkyl groups such as methyl, ethyl and the like; and alkylcarboxyloxyalkyl groups such as acetoxymethyl, propionyloxymethyl, pivaloyloxymethyl and the like.

The protecting group for amino group, aminoalkyl group, alkylamino group and alkylaminoalkyl group includes, for example, pharmaceutically acceptable amino-protecting groups easily eliminated in living body. Specific examples thereof are acyl groups such as formyl, acetyl and the like.

The protecting group for hydroxyl group and hydroxyalkyl group includes, for example, pharmaceutically acceptable hydroxyl-protecting groups easily eliminated in living body. Specific examples thereof are acyl groups such as formyl, acetyl and the like; and alkoxycarbonyloxyalkyl groups such as ethoxycarbonyloxyethyl and the like.

Specific compounds preferably used as the drug in the present invention include those compounds wherein a basic group is bonded to the 7-position of naphthyridine or quinoline or to the 10-position of benzoxazine or benzothioxazine, and include, for example, the following compounds.

1-Ethyl-6-fluoro-1,4-dihydro-4-oxo-7-(1-piperazinyl)-1,8-naphthyridine-3-carboxylic acid 7-(3-Amino-1-pyrrolidinyl)-1-ethyl-6-fluoro-1,4-dihydro-4-oxo-1,8-naphthyridine-3-carboxylic acid 7-(3-Amino-1-pyrrolidinyl)-1-cyclopropyl-6-fluoro-1,4-dihydro-4-oxo-1,8-naphthyridine-3-carboxylic acid 7-(3-Amino-4-methyl-1-pyrrolidinyl)-1-cyclopropyl-6-fluoro-1,4-dihydro-4-oxo-1,8,-naphthyridine-3-carboxylic acid 1-Cyclopropyl-6-fluoro-7-(3-methylamino-1-pyrrolidinyl)-1,4-dihydro-4-oxo-1,8-naphthyridine-3-carboxylic acid 7-(3-Amino-3-methyl-1-pyrrolidinyl)-1-cyclopropyl-6-fluoro-1,4-dihydro-4-oxo-1,8-naphthyridine-3-carboxylic acid 1-Cyclopropyl-6-fluoro-7-(1-piperazinyl)-1,4-dihydro-4-oxo-1,8-naphthyridine-3-carboxylic acid 7-(cis-3-Aminomethyl-4-chloro-1-pyrrolidinyl)-1-cyclopropyl-6-fluoro-1,4-dihydro-4-oxo-1,8-naphthyridine-3-carboxylic acid 7-(3-Amino-1-pyrrolidinyl)-1-(2,4-difluorophenyl)-6-fluoro-1,4-dihydro-4-oxo-1,8-naphthyridine-3-carboxylic acid (tosufloxacin)

1-Ethyl-6-fluoro-7-(1-piperazinyl)-1,4-dihydro-4-oxoquinoline-3-carboxylic acid

1-Ethyl-6,8-difluoro-7-(3-methyl-1-piperazinyl)-1,4-dihydro-4-oxoquinoline-3-carboxylic acid 1-(2-Fluoroethyl)-6,8-difluoro-7-(4-methyl-1-piperazinyl)-1,4-dihydro-4-oxoquinoline-3-carboxylic acid 5-Amino-1-cyclopropyl-7-(3,5-dimethyl-1-piperazinyl)-6,8-difluoro-1,4-dihydro-4-oxoquinoline-3-carboxylic acid 7-(3-Amino-1-pyrrolidinyl)-1-cyclopropyl-6,8-difluoro-1,4-dihydro-4-oxoquinoline-3-carboxylic acid 7-(3-Aminomethyl-1-morpholino)-1-cyclopropyl-6,8-difluoro-1,4-dihydro-4-oxoquinoline-3-carboxylic acid 1-Cyclopropyl-6-fluoro-7-(1-piperazinyl)-1,4-dihydro-4-oxoquinoline-3-carboxylic acid 1-Cyclopropyl-6-fluoro-5-methyl-7-(3-methyl-1-piperazinyl)-1,4-dihydro-4-oxoquinoline-3-carboxylic acid 6-Fluoro-1-(2,4-difluorophenyl)-7-(3-methyl-1-piperazinyl)-1,4-dihydro-4-oxoquinoline-3-carboxylic acid 5-Amino-1-cyclopropyl-7-(3-ethylaminomethyl-1-pyrrolidinyl)-6,8-difluoro-1,4-dihydro-4-oxoquinoline-3-carboxylic acid 1-Cyclopropyl-7-(3-ethylaminomethyl-1-pyrrolidinyl)-5,6,8-trifluoro-1,4-dihydro-4-oxoquinoline-3-carboxylic acid 1-Ethyl-6-fluoro-7-(4-methyl-1-piperazinyl)-1,4-dihydro-4-oxoquinoline-3-carboxylic acid 1-Cyclopropyl-7-(3,5-dimethylpyridine-1-yl)-6-fluoro-4-oxoquinoline-3-carboxylic acid 9-Fluoro-3-methyl-10-(4-methyl-1-piperazinyl)-7-oxo-2,3-dihydro-7H-pyrido[1,2,3-de][1,4]benzoxazine-6-carboxylic acid 10-(1-Aminocyclopropyl)-9-fluoro-3-methyl-7-oxo-2,3-dihydro-7H-pyrido[1,2,3-de][1,4]benzoxazine-6-carboxylic acid (S)-9-Fluoro-3-methyl-10-(4-methyl-1-piperazinyl)-7-oxo-2,3-dihydro-7H-pyrido[1,2,3-de][1,4]benzoxazine-6-carboxylic acid (S)-10-(1-Aminocyclopropyl)-9-fluoro-3-methyl-7-oxo-2,3-dihydro-7H-pyrido[1,2,3-de][1,4]benzoxazine-6-carboxylic acid The drug is used in an amount for treating oral diseases. The amount can be determined appropriately.

The hydrophobic ointment base used in the present invention includes gelled hydrocarbons such as plastibase, petrolatum, paraffin, silicone, and the like. Gelled hydrocarbons such as plastibase are preferred.

These hydrophobic ointment bases may be used singly or in combination of two or more.

The amount of the hydrophobic ointment base used is not particularly restricted, but falls within the range of 50–95% by weight, preferably 75–90% by weight based on the total weight of the ointment.

The adhesive substance used in the present invention includes alginic acid derivatives such as propylene glycol alginate and the like; cellulose derivatives such as hydroxypropyl cellulose, hydroxypropyl methyl cellulose, methyl cellulose and the like; synthetic polymer compounds such as polyvinyl alcohol, polyvinyl pyrrolidone and the like; pullulan; and so forth. Cellulose derivatives such as hydroxypropyl methyl cellulose and the like are preferred.

These adhesive substances may be used singly or in combination of two or more.

The amount of the adhesive substance used is not particularly restricted, but falls within the range of 5–50% by weight, preferably 10–15% by weight based on the total weight of the ointment.

The aluminum compound used in the present invention includes inorganic aluminum compounds such as aluminum chloride, aluminum sulfate, aluminum oxide, aluminum hydroxide, potassium aluminum sulfate, sodium aluminum sulfate, ammonium aluminum sulfate and the like; and salts between aluminum and a pharmaceutically acceptable carboxylic acid such as aluminum lactate and the like. Potassium aluminum sulfate and aluminum lactate are preferred.

These aluminum compounds may be hydrates or anhydrides.

These aluminum compounds may be used singly or in combination of two or more.

The amount of the aluminum compound used is not particularly restricted, but falls within the range of 0.1–10% by weight, preferably 0.2–4.0% by weight based on the total weight of the ointment.

To the sustained-release oral ointment according to the present invention may be added known additives such as flavors, spices, coloring agent, surfactant and the like unless the addition adversely affects the present invention.

The sustained-release oral ointment according to the present invention can be used by the same application method as for known oral ointments. For example, the ointment can be injected into a periodontal pocket or can be directly applied on an affected part.

The method for producing the sustained-release oral ointment of the present invention has no particular restriction. The ointment can be produced by a method ordinarily used in the field or by an appropriate combination of two or more. Specifically, the ointment can be produced by simple mixing of individual components, i.e. a hydrophobic ointment base, an adhesive substance, an aluminum compound and a drug.

Next, description is made on the dissolution test conducted for the sustained-release oral ointment of the present invention.

[Dissolution test]

In order to confirm the sustained-release properties of the sustained-release oral ointment of the present invention, a test was conducted using a test apparatus shown in FIG. 1. Specifically, about 0.5 g of a sustained-release oral ointment was spread on the upper surface of the bottom 1 (for ointment applying thereon) of the test apparatus in a disc shape 2 of 29 mm in diameter. On the spread ointment were placed a screen 3 and an o-ring 4. Thereon was placed and fixed a two ends-open cylinder 5 (for solvent holding) having a thick wall. Into the cylinder for solvent holding was injected a solvent at a rate of 5 ml/hr. The test was conducted at 37°±0.5° C. From the start of the test to 7th hours, solvent exchange was made at intervals of one hour by decantation and the concentration of drug was measured by spectrophotometry. In the period of 7th to 24th hour, the whole apparatus was immersed in 85 ml of a new solvent at the 7th hour from the start of the test; thereafter, solvent exchange with 120 ml of a new solvent was made at the 24th hour and the 48th hour from the start of the test; and the concentration of drug was measured in the same manner. After 7 hours from the start of the test, the whole apparatus was immersed in the solvent and the test was conducted. As the solvent, there was used an artificial saliva (pH 7.0) and, as the sample, there were used sustained-release oral ointments of Examples 1, 2, 3 and 4 and Comparative Examples 1 and 2.

The results of the above test are shown in FIG. 2 and FIG. 3, respectively.

As shown in the results, the sustained-release oral ointment of the present invention exhibits such advantages that the drug contained in the ointment is dissolved easily and released over a long period of time. Further, the sustained-release oral ointment of the present invention is superior in that the ointment, as compared with the ointments of Comparative Examples containing no aluminum compound, releases the drug at a high concentration and permits the utilization of the drug at a high utilization ratio.

BRIEF DESCRIPTION OF THE DRAWINGS

FIG. 1 is a drawing showing an apparatus used for dissolution test.

BEST MODE FOR CARRYING OUT THE INVENTION

Figure 2:
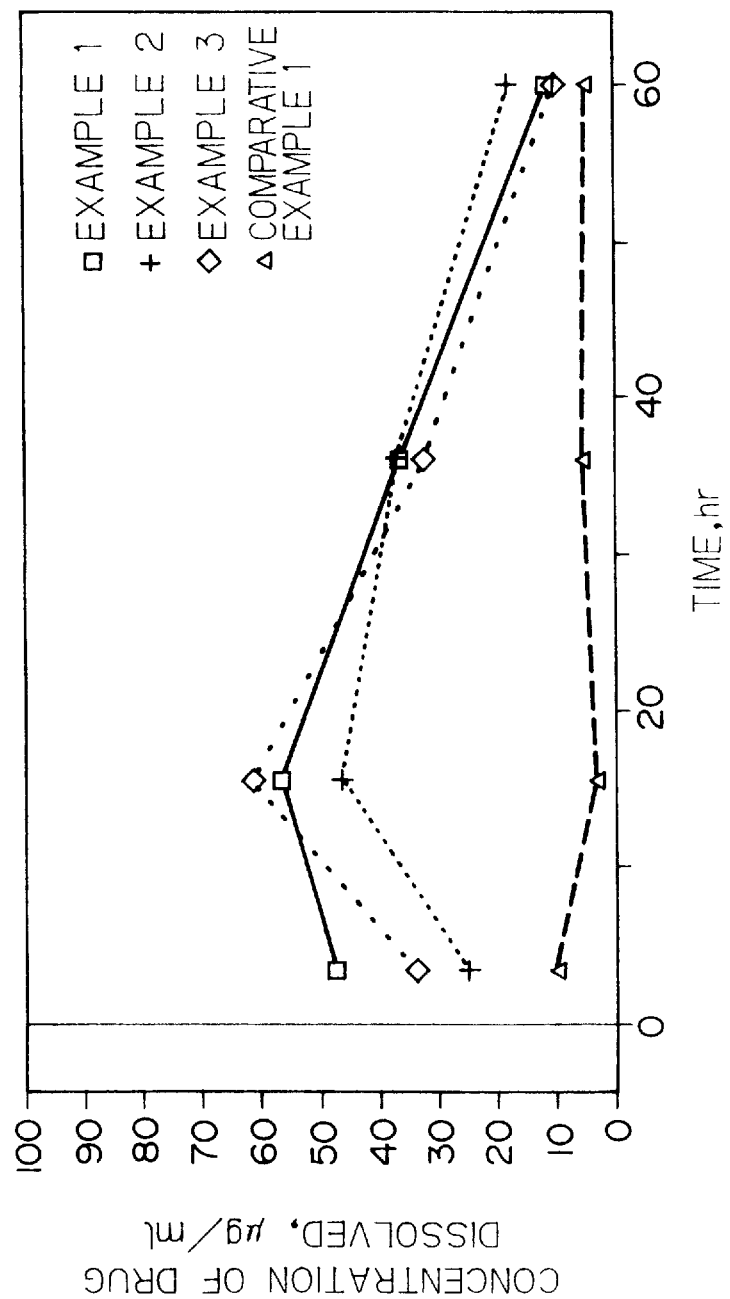
FIG. 2 is a graph showing the results of dissolution test (the results of concentration of drug dissolved) of the sustained-release oral ointments obtained in Examples 1, 2 and 3 and Comparative Example 1.
Figure 3:
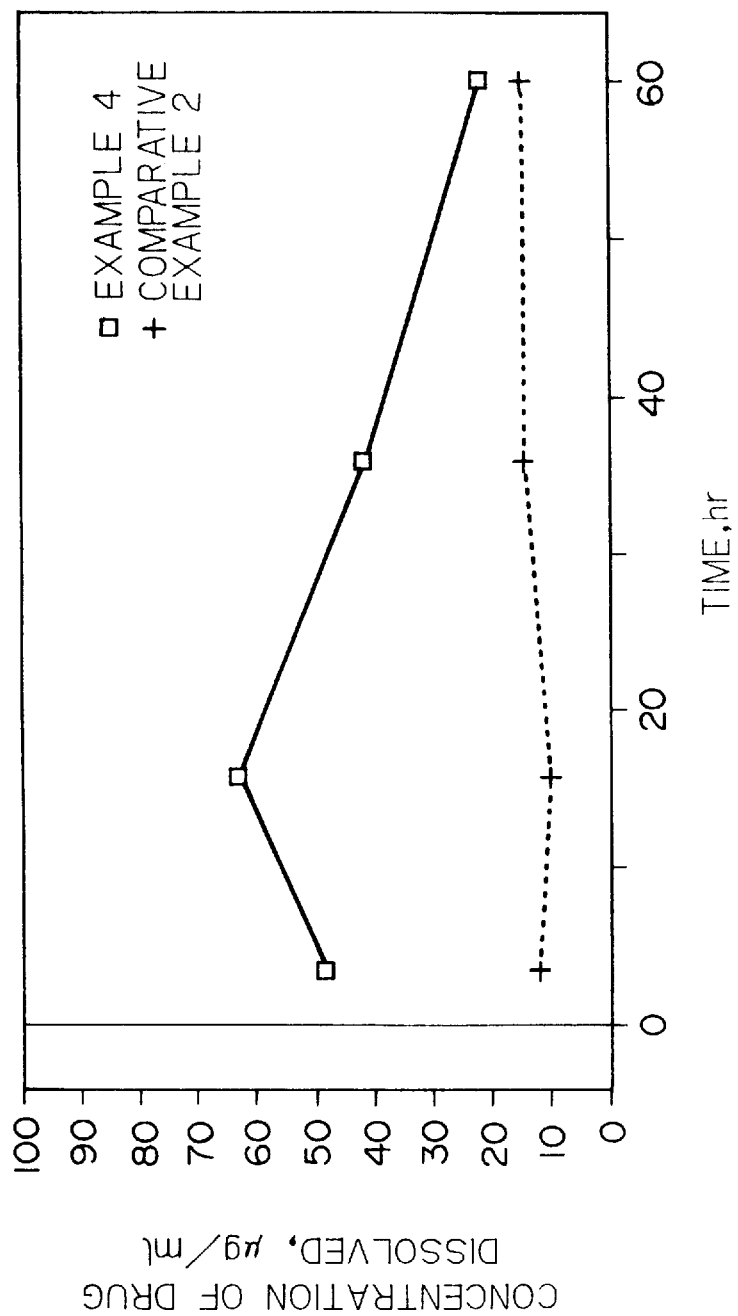
FIG. 3 is a graph showing the results of dissolution test (the results of concentration of drug dissolved) of the sustained-release oral ointments obtained in Example 4 and Comparative Example 2.

Next, the method for producing the sustained-release oral ointment of the present invention is described specifically by way of Examples. However, the present invention is not restricted thereto.

Example 1

16.56 g of a plastibase was uniformly mixed with 0.80 g of tosufloxacin tosylate, 0.64 g of potassium aluminum sulfate and 2.00 g of hydroxypropyl methyl cellulose to obtain a sustained-release oral ointment.

Example 2

16.90 g of a plastibase was uniformly mixed with 0.80 g of tosufloxacin tosylate, 0.35 g of dry potassium aluminum sulfate and 2.00 g of hydroxypropyl methyl cellulose to obtain a sustained-release oral ointment.

Example 3

16.80 g of a plastibase was uniformly mixed with 0.80 g of tosufloxacin tosylate, 0.40 g of aluminum lactate and 2.00 g of hydroxypropyl methyl cellulose to obtain a sustained-release oral ointment.

Example 4

The same procedure as in Example 2 was repeated except that the tosufloxacin tosylate used in Example 2 was replaced by 0.80 g of (S)-10-(1-aminocyclopropyl)-9-fluoro-3-methyl-7-oxo-2,3-dihydro-7H-pyrido[1,2,3-de][1,4]benzoxazine-6-carboxylic acid to obtain a sustained-release oral ointment.

Comparative Example 1

16.20 g of a plastibase was uniformly mixed with 0.80 g of tosufloxacin tosylate and 3.00 g of hydroxypropyl methyl cellulose to obtain a sustained-release oral ointment.

Comparative Example 2

17.20 g of a plastibase was uniformly mixed with 0.80 g of (S)-10-(1-aminocyclopropyl)-9-fluoro-3-methyl-7-oxo-2,3-dihydro-7H-pyrido[1,2,3-de][1,4]benzoxazine-6-carboxylic acid and 2.00 g of hydroxypropyl methyl cellulose to obtain a sustained-release oral ointment.

INDUSTRIAL APPLICABILITY

The sustained-release oral ointment of the present invention exhibits such advantages that the drug is dissolved easily, is released over a long period of time and is utilized at a very high utilization ratio, and that the ointment can be applied even to a periodontal pocket.

We claim:

1. A sustained-release oral ointment which comprises a hydrophobic ointment base, an adhesive substance, an aluminum compound and a drug.

2. A sustained-release oral ointment according to claim 1, wherein the drug is a compound represented by the following general formula:

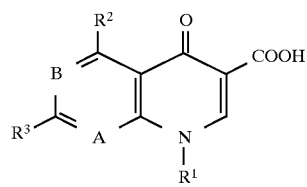

wherein $R^1$ represents a substituted or unsubstituted alkyl, alkenyl, cycloalkyl, aryl or heterocyclic group; $R^2$ represents a hydrogen atom, a halogen atom, an alkyl group, an alkoxy group, a protected or unprotected hydroxyl, amino or alkylamino group or a dialkylamino group; $R^3$ represents a substituted or unsubstituted cycloalkyl, vinyl or cyclic amino group;

represents a group

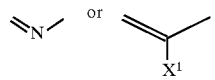

wherein $X^1$ represents a hydrogen atom or a halogen atom, or alternatively, forms, together with $R^1$, a group represented by the formula:

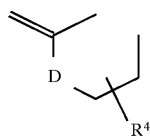

wherein $R^4$ represents a hydrogen atom or an alkyl group, and D represents an oxygen atom or a sulfur atom; and

represents a group represented by

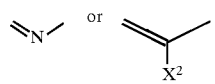

wherein $X^2$ represents a hydrogen atom or a halogen atom.

* * * * *